US00PP21334P2

(12) United States Plant Patent

Waterer et al.

(10) Patent No.: US PP21,334 P2

(45) Date of Patent: Sep. 28, 2010

(54) *GERANIUM* PLANT NAMED 'LILAC ICE'

(50) Latin Name: ***Geranium wallichianum*×*Geranium himalayense***

Varietal Denomination: Lilac Ice

(76) Inventors: Thomas Waterer, 41 Alder Lane, Balsall Common, Coventry CV&7DZ (GB); Michael Hugo Waterer, Whincote, Thorndon Cross, Okehampton, Devon EX20 4NF (GB)

( * ) Notice: Subject to any disclaimer, the term of this patent is extended or adjusted under 35 U.S.C. 154(b) by 0 days.

(21) Appl. No.: 12/315,315

(22) Filed: Dec. 2, 2008

(51) Int. Cl.
*A01H 5/00* (2006.01)

(52) U.S. Cl. ..... Plt./324

(58) Field of Classification Search ..... Plt./324
See application file for complete search history.

*Primary Examiner*—June Hwu
(74) *Attorney, Agent, or Firm*—C. A. Whealy

(57) ABSTRACT

A new and distinct cultivar of *Geranium* plant named 'Lilac Ice', characterized by its compact, upright and outwardly spreading plant habit; vigorous growth habit; deeply dissected leaves; freely and continuous flowering habit; large single light purple-colored flowers with red purple-colored venation; long flowering period; and good garden performance.

1 Drawing Sheet

Botanical designation: *Geranium wallichianum*×*Geranium himalayense.*

Cultivar denomination: 'Lilac Ice'.

BACKGROUND OF THE INVENTION

The present invention relates to a new and distinct cultivar of *Geranium* plant, botanically known as *Geranium wallichianum*×*Geranium himalayense*, and hereinafter referred to by the name 'Lilac Ice'.

The new *Geranium* plant is a naturally-occurring whole plant mutation of *Geranium wallichianum*×*Geranium himalayense* 'Rozanne', disclosed in U.S. Plant Pat. No. 12,175. The new *Geranium* was discovered and selected by the Inventors as a single flowering plant from within a population of plants of 'Rozanne' in a controlled greenhouse environment in Bressingham, United Kingdom in June, 2006.

Asexual reproduction of the new *Geranium* plant by tissue culture in a controlled environment in Bressingham, United Kingdom since July, 2006, has shown that the unique features of this new *Geranium* are stable and reproduced true to type in successive generations.

SUMMARY OF THE INVENTION

Plants of the new *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Lilac Ice'. These characteristics in combination distinguish 'Lilac Ice' as a new and distinct cultivar of *Geranium*:

1. Compact, upright and outwardly spreading plant habit.
2. Vigorous growth habit.
3. Deeply dissected leaves.
4. Freely and continuous flowering habit.
5. Large single light purple-colored flowers with red purple- colored venation.
6. Long flowering period.
7. Good garden performance.

Plants of the new *Geranium* differ primarily from plants of the parent, 'Rozanne', in flower color as plants of 'Rozanne' have violet blue-colored flowers with white-colored centers and purple violet-colored venation.

Plants of the new *Geranium* can be compared to plants of *Geranium wallichianum* 'Buxton's Variety', not patented. In side-by-side comparisons conducted in Bressingham, United Kingdom, plants of the new *Geranium* differed primarily from plants of 'Buxton's Variety' in flower color as plants of 'Buxton's Variety' had light violet blue-colored flowers with white-colored centers.

BRIEF DESCRIPTION OF THE PHOTOGRAPHS

The accompanying colored photographs illustrate the overall appearance of the new *Geranium*, showing the colors as true as it is reasonably possible to obtain in colored reproductions of this type.

Colors in the photographs may differ slightly from the color values cited in the detailed botanical description which accurately describe the colors of the new *Geranium.*

The photograph at the bottom of the sheet comprises a top perspective view of a typical flowering plant of 'Lilac Ice' grown in a container.

The photograph at the top of the sheet is a close-up view of typical flowers of 'Lilac Ice'.

DETAILED BOTANICAL DESCRIPTION

The aforementioned photographs and following observations, measurements and values describe plants grown in one-gallon containers in Lancaster, Pa. in a polyethylene-covered greenhouse during the late spring. During the production of the plants, day temperatures ranged from 1.7° C. to 21° C. and night temperatures ranged from 1.7° C. to 13° C. Plants had been growing for 12 months when the photographs and the description were taken. In the detailed description, color references are made to The Royal Horticultural Society Colour Chart, 2007 Edition, except where general terms of ordinary dictionary significance are used.

Botanical classification: *Geranium wallichianum*×*Geranium himalayense* 'Lilac Ice'.

Parentage: Naturally-occurring whole plant mutation of *Geranium wallichianum*×*Geranium himalayense* 'Rozanne', disclosed in U.S. Plant Pat. No. 12,175.

Propagation:

*Type.*—By tissue culture.

*Time to initiate roots.*—About 15 days at 25° C. air temperature.

*Time to produce a rooted young plant.*—About 45 days at 25° C. air temperature.

*Root description.*—Medium to thin in thickness, fleshy to fibrous; 174A in color.

*Rooting habit.*—Freely branching; moderately dense.

Plant description:

*General appearance and habit.*—Hardy herbaceous perennial; compact, upright and outwardly spreading plant habit; clumping and low spreading, rounded; vigorous growth habit.

*Plant height.*—About 18 cm.

*Plant width.*—About 42 cm.

Lateral branches:

*Branching habit.*—Freely basal branching habit; pinching is not required; about twelve lateral branches develop per plant.

*Length.*—About 18 cm.

*Diameter: About* 3.5 cm.

*Internode length.*—About 5 cm.

*Strength.*—Strong.

*Aspect.*—Lateral branches grow outwardly to spreading horizontally.

*Texture.*—Pubescent.

*Color.*—Close to 145B to 145C.

Foliage description:

*Arrangement.*—Opposite, simple.

*Length.*—About 7.4 cm.

*Width.*—About 7.5 cm.

*Shape.*—Deeply palmately incised with five main dissected lobes.

*Apex.*—Mucronate.

*Base.*—Sagittate.

*Margin.*—Palmately cleft; lobes biserrate and sinuate.

*Venation pattern.*—Palmate; reticulate.

*Texture, upper and lower surfaces.*—Pubescent.

*Color.*—Developing leaves, upper and lower surfaces: Close to 146B. Fully developed leaves, upper surface: Close to 137A; venation, close to 145A. Fully developed leaves, lower surface: Close to 146B; venation, close to 146B.

*Petiole.*—Length: About 8.5 cm. Diameter: About 2 mm. Texture, upper and lower surfaces: Pubescent. Color, upper and lower surfaces: Close to 146D.

Flower description:

*Flower arrangement/habit.*—Single rotate flowers arranged in axillary clusters with usually two flowers per cluster; freely flowering habit with about 60 flowers developing per plant; flowers face upright to outwardly.

*Fragrance.*—Not detected.

*Flowering season.*—In Lancaster, Pa., plants begin flowering about 10 to 14 weeks after planting; in the garden, flowering is continuous during the early summer.

*Flower longevity.*—Flowers last about four to five days on the plant; corolla not persistent, corona persistent.

*Flower buds.*—Length: About 1.4 cm. Diameter: About 7 mm Shape: Ovoid with pointed sepal apices. Color: Close to 84A.

*Flower diameter.*—About 3.6 cm.

*Flower depth.*—About 2 cm.

*Petals.*—Quantity per flower: Five in a single whorl. Length: About 2.2 cm. Width: About 1.8 cm. Shape: Obcordate. Apex: Cordate to rounded. Base: Acute. Margin: Entire. Texture, upper and lower surfaces: Smooth, glabrous; satiny. Color: When opening, upper surface: Close to 85A. When opening, lower surface: Close to 85C. Fully opened, upper surface: Close to 76A to 76B; venation, close to 71A; color becoming closer to 76B to 76C with development. Fully opened, lower surface: Close to 76B; towards the base, close to NN155D; color becoming closer to 76B to 76C with development.

*Sepals.*—Quantity per flower: Five, arranged in a single whorl. Length: About 1.4 cm. Width: About 5 mm. Shape: Elliptical. Apex: Acuminate. Base: Truncate. Margin: Entire. Texture, upper surface: Smooth, glabrous. Texture, lower surface: Pubescent. Color, upper and lower surfaces: Close to 146B.

*Peduncles* (*flower cluster stalk*).—Length: About 13 cm. Diameter: About 1.5 mm. Strength: Strong. Aspect: About 30° to 45° from the stem axis. Texture: Pubescent. Color: Close to 145A.

*Pedicels* (*individual flower stalk*).—Length: About 3.2 cm. Diameter: About 1 mm. Strength: Strong. Aspect: About 45° from the peduncle axis. Texture: Pubescent. Color: Close to 146D.

*Reproductive organs.*—Androecium: Stamen quantity per flower: About ten. Filament length: About 7 mm. Filament color: Close to N78C. Anther length: About 2.5 mm. Anther shape: Narrowly lanceolate. Anther color: Close to 79A. Pollen amount: Scarce. Pollen color: Close to 151D. Gynoecium: Pistil quantity per flower: One. Pistil length: About 1.3 cm. Stigma shape: Five-parted. Stigma color: Close to 71A. Style length: About 4 mm. Style color: Close to 71C. Ovary color: Close to 147B to 147C.

*Seed/fruits.*—Seed and fruit development have not been observed.

Disease/pest resistance: Plants of the new *Geranium* have been observed to be tolerant to Mildews. Plants of the new *Geranium* have not been observed to resistant to pests and other pathogens common to *Geraniums.*

Garden performance: Plants of the new *Geranium* have exhibited good garden performance and to tolerate rain and wind and have been observed to be suitable for USDA Zones 5 to 8 and AHS Heat Zones 2 to 12.

It is claimed:

1. A new and distinct *Geranium* plant named 'Lilac Ice' as illustrated and described.

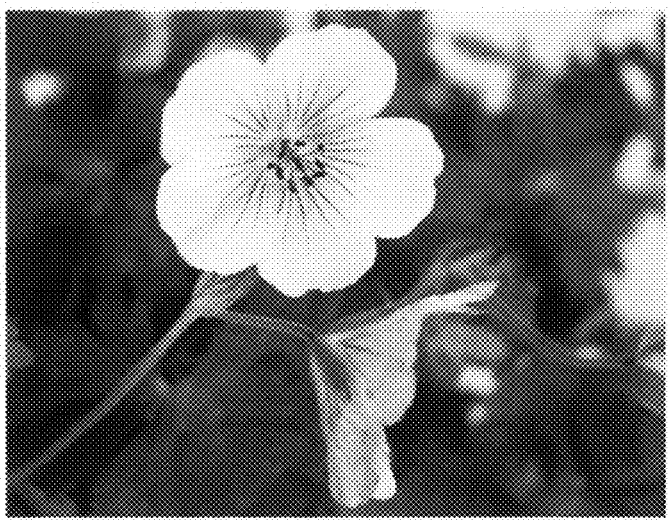
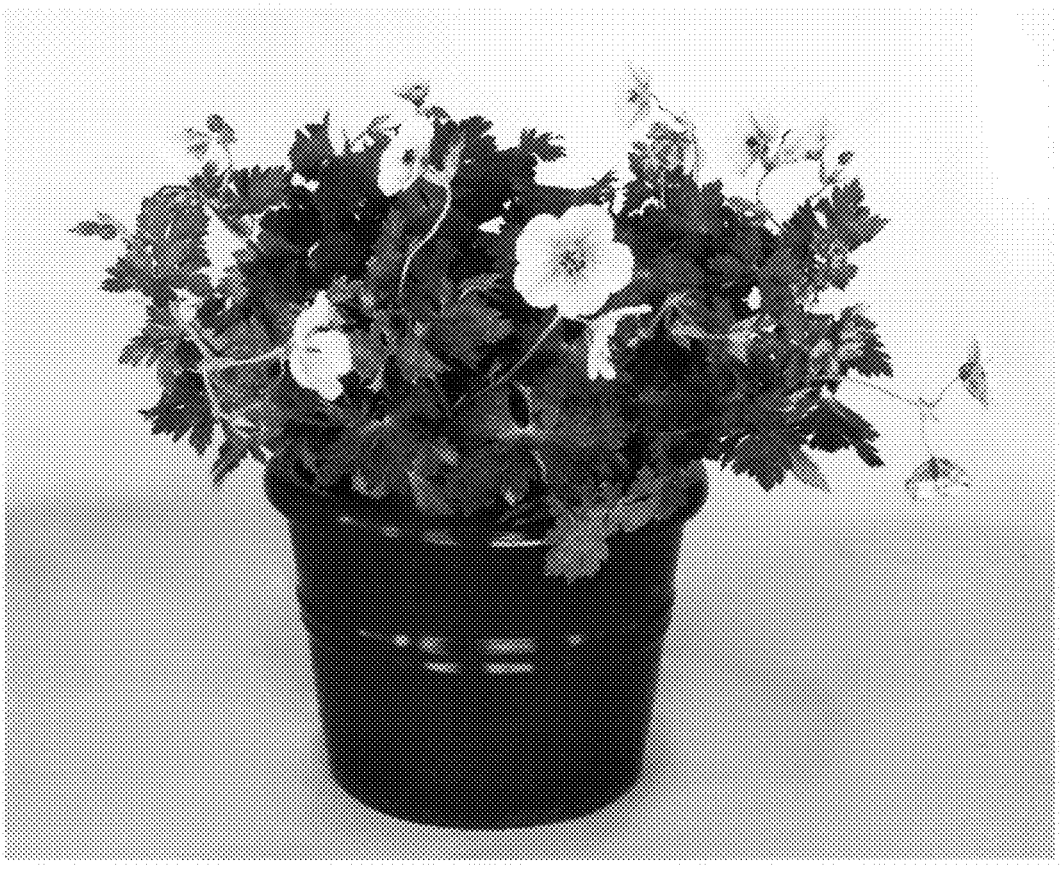

* * * * *